United States Patent
Schwartz et al.

[11] Patent Number: 5,414,778
[45] Date of Patent: May 9, 1995

[54] DYNAMIC FLUID LEVEL AND BUBBLE INSPECTION FOR QUALITY AND PROCESS CONTROL

[76] Inventors: Nira Schwartz; Arie Shahar; Richard Woods, all of 2800 Plaza Del Amo #187, Torrance, Calif. 90503

[21] Appl. No.: 157,734

[22] Filed: Nov. 24, 1993

[51] Int. Cl.6 ............................................ G06K 9/00
[52] U.S. Cl. .......................... 382/142; 250/223 B; 356/427
[58] Field of Search .............. 382/8, 18, 51; 348/127, 348/128; 209/522–528; 250/900, 223 B; 356/240, 427

[56] References Cited

U.S. PATENT DOCUMENTS

| | | | |
|---|---|---|---|
| 3,232,429 | 2/1966 | Norwich | 209/524 |
| 4,050,824 | 9/1977 | Woodrow et al. | 356/427 |
| 4,172,524 | 10/1979 | Holm et al. | 209/524 |
| 4,365,304 | 12/1982 | Ruhman et al. | 382/51 |
| 4,429,414 | 1/1984 | Asakawa | 382/30 |
| 4,606,065 | 8/1986 | Beg et al. | 382/18 |
| 4,637,054 | 1/1987 | Hashim | 382/8 |
| 4,736,851 | 4/1988 | Ricros et al. | 209/524 |
| 4,915,237 | 4/1990 | Chang et al. | 209/524 |
| 5,007,096 | 4/1991 | Yoshida | 382/8 |
| 5,052,044 | 9/1991 | Gaborski | 382/32 |
| 5,072,108 | 12/1991 | Ishikawa | 356/427 |
| 5,073,708 | 12/1991 | Matsumoto et al. | 356/427 |
| 5,136,661 | 4/1992 | Kobayasi et al. | 382/48 |
| 5,204,911 | 4/1993 | Schwartz et al. | 382/8 |

*Primary Examiner*—Yon J. Couso
*Assistant Examiner*—Gerard Del Rosso

[57] ABSTRACT

Fast image acquisition and image process control can be used to advantage to measure dynamic and transient phenomena. This technique can distinguish fluid from bubbles by modifying the image's gray levels. The technique is used for detecting fluid levels and bubbles, by counting image pixels dedicated to bubbles or to fluid along vertical or horizontal lines within the image. The rate of change of fluid level and the amount of bubbles with time indicate leakage in containers while they are in a dynamic state. The inspection of transient phenomena during a dynamic state gives an indication of the final quality and quantity of a product inside a container. It also provides a good feedback for the determination of fill nozzle operation, with the advantage of easy calibration and adjustment for the right amount of bubbles within the container. The application is highly beneficial in the beer and soft drink industry where the taste of the product is highly influenced by the amount of bubbles within the container.

20 Claims, 3 Drawing Sheets

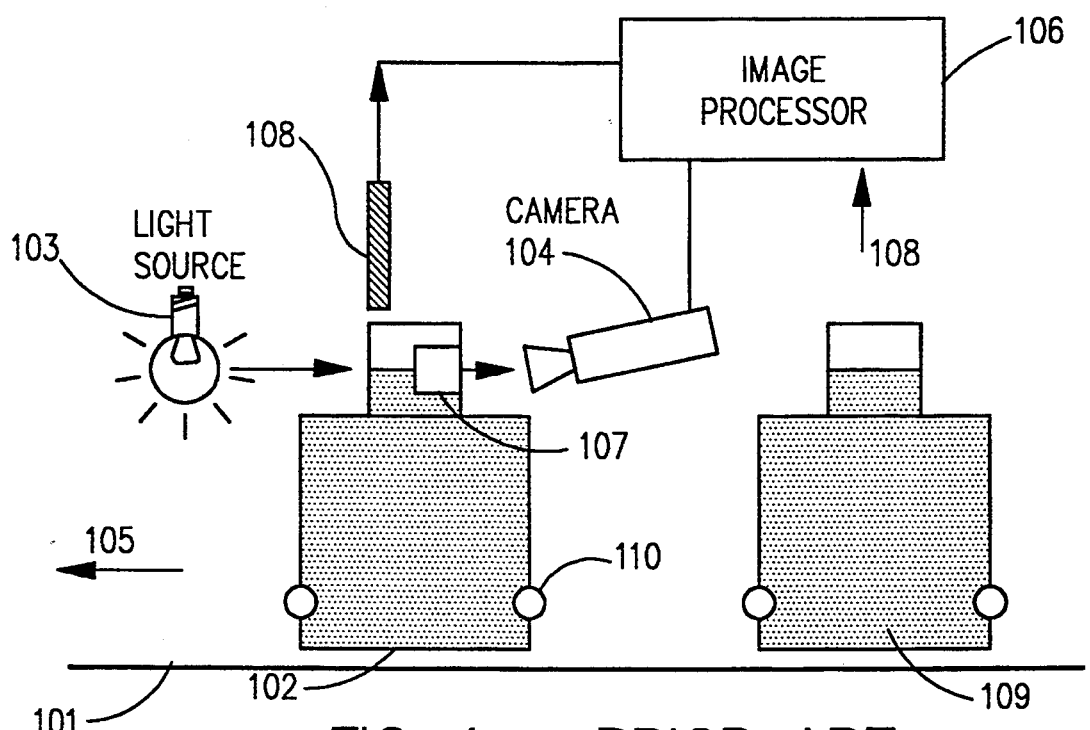
FIG. 1 — PRIOR ART
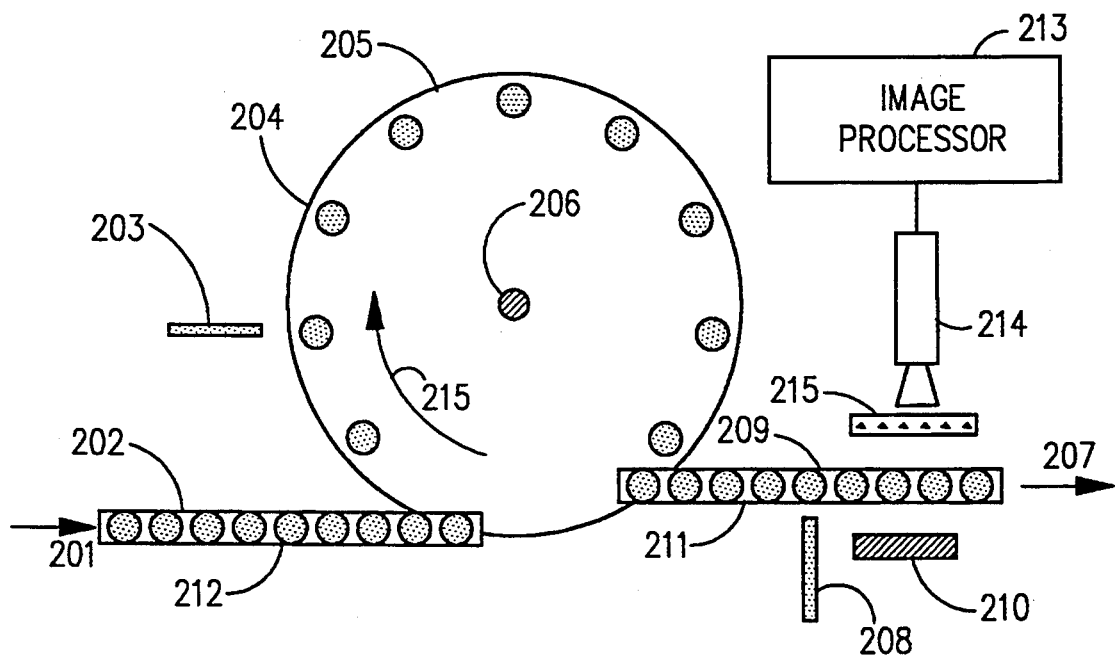
FIG. 2

DYNAMIC FLUID LEVEL AND BUBBLE INSPECTION FOR QUALITY AND PROCESS CONTROL

BACKGROUND OF THE INVENTION

1. Field of the Invention

Generally, the field of the invention relates to quality and process control, particularly to the inspection of fluid levels in containers as well as bubbles (gas) in the fluid.

2. Prior Art

An known bottle or container inspection system is designed to inspect containers while they are moving on a production line and predict container pressure as a function of fluid level fluctuations with and without squeezing the container. The system contains a light source and uses a back light having a unique wavelength to illuminate the containers being inspected. Images of the inspected containers are stored in a computer's memory for analysis by means of an algorithm. The algorithm is also stored in the computer's memory. The system is shown in FIG. 1 and is described our copending application, Ser. No. 07/911,130, filed Sep. 7, 1992. To obtain inspection of the bottle's fluid level, a dynamic state of the liquid in the bottles is created by squeezing the bottles. However this technique can be applied only to soft bottles, e.g., of plastic. This method will not work for non-squeezable bottles, e.g., of glass.

OBJECTS AND ADVANTAGES

Accordingly one object of the invention to provide an improved way to predict final fluid level and the amount of dissolved gasses in containers while they are moving on a production line. Another object is to be able to perform the foregoing without having to squeeze the bottles. Therefore this technique can be used to inspect glass containers as well.

Another object is to indicate the quality of the fluid within the container and if the cap is properly sealed. Still another object of the invention is to predict the liquid viscosity as a function of the rate bubbles are dissolved.

Other objects and advantages are to provide a correlation between the fill nozzle on a filling carousel and the inspected container for easy nozzle adjustment for the right amount of fluid and bubbles inside a container, thereby to provide an automatic alarm if one of the nozzles on the carousel is off calibration.

Further objectives and advantages will become apparent from a consideration of the ensuing description and accompanying drawings.

BRIEF DESCRIPTION OF DRAWINGS

FIG. 1 is a schematic view of a prior-art quality-control system employing an image processor for inspecting of squeezed containers.

FIG. 2 is a schematic view of a filling fluid system employing an image processor according to the invention.

DRAWING REFERENCE NUMERALS

Figure 3:
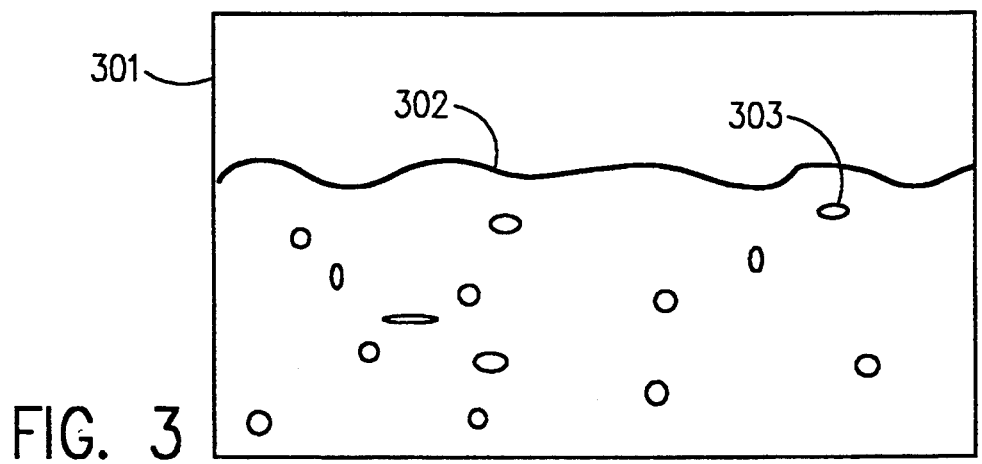
FIG. 3 is a view of a camera's field of view showing a fluid level and bubbles within the fluid in accordance with the invention.

101 Conveyor
102 Container
103 Light Source
104 Camera
105 Direction of Motion
106 Image Processor
107 Container Neck
108 Bottle Sensor
109 Container
203 Container Sensor
204 Nozzles
205 Filling Carousel
206 Carousel's Axis of Rotation
207 Output Conveyor
208 Container Sensor
209 Camera
210 Light Source
211 Output Conveyor
212 Conveyor
213 Image Processor
213 Camera
215 Direction of Rotation of the Carousel

GENERAL SUMMARY OF THE METHOD

The method of the invention comprises the following sequential steps:

(1) The fluid level inside a container is scanned optically while the fluid is in a dynamic state. The scan produces an image having gray levels.

(2) The gray levels in the image are modified.

(3) The fluid height is measured several times.

(4) The amount of bubbles (gas) within the fluid is measured several times.

(5) The data from the measured fluid height (3) and bubble measurement (4) is correlated to the carousel's filling nozzle using a mathematical function (6) The fluid height, amount of bubbles, rate of change of fluid height, and bubbles are analyzed and compared with the dynamic range and behavior of an acceptable product.

(7) The container is tested for leaks by analyzing the dynamic behavior of the fluid and the bubbles.

Each of the above steps will now be considered separately in detail.

FIG. 1—Product Inspection System—Prior Art

FIG. 1 shows a prior-art system for analyzing fluid (beer, soft drinks, water, liquid medicine) inside containers. The fluid is in a dynamic state as a result of squeezing the container. The system of FIG. 1 can be placed at any distance after the filling carousel.

The system of FIG. 1 is used as follows: Assume that containers 102 and 109 are to be inspected. The containers move on conveyor 101 in a direction 105. The containers are illuminated by light source 103, and the container or product images are taken by a sensor 104, which is an industrial camera. A dynamic state of the fluid in the containers is created by squeezing the bottles between two bars 110. The images from the inspected containers are sent to an image processor 106 and saved in a memory of processor 106. A suitable image processor 106 is produced by Imaging Technology Inc., Woburn, Mass., Model 150/151 and also Model 15040. This processor, together with the camera, is able to acquire images, store acquired images in it memory, modify the images' gray levels with the use of its lookup tables, add and subtract images, count pixels with specific gray levels by the use of the histogram function, and invoke mathematical functions on any data saved in memory. It is a fast convenient tool for image processing.

Image processor 106 contains several memory boards (not shown). Each board is large enough to save several images. The stored images include an image of product and the result of a superposition process, i.e., the superposed images of the product and a template which has also been stored in the memory of processor 106.

Processor 106 also includes hardware lookup tables (not shown). Those tables are also used for modifying gray levels of the product image according to a preloaded (at the startup cycle) conversion table.

Processor 106 also contains a hardware board (not shown) which includes a microprocessor for calculating histograms of images while they are saved in the memory. The motherboard of the processor unit includes a very fast computer, such as a Motorola 68040 microprocessor and an onboard RAM. This board includes an algorithm for processing the histogram vector values and making inspection decisions.

The system of prior-art FIG. 1 operates as follows: The gray levels of the product image are shifted according to the lookup tables before saving in memory takes place. Processor 106 counts the number of pixels related to gray levels along vertical or horizontal lines. This count can be done by the software algorithm supplied with processor 106 or as a part of the system hardware. The pixels inside a predefined window within the modified product are also counted. The count values are stored in the memory of the computer for future analysis.

The camera's field of view is part of the container's neck, as shown at 107. It is also possible to define a larger field of view that includes the full container neck, or even the container's wall.

A bottle sensor 108 is connected to processor 106 for triggering image acquisition.

FIG. 2—Filling Carousel

The difference between prior-art inspection systems and the present inspection system relates to the inspection of non-squeezable containers. Also, while we still use an image processor 213 identical to the prior-art processor 106 (FIG. 1), we measure different physical phenomena. In both cases the system counts pixels. However in the present inspection system the system counts, in the container's image, pixels which display different physical phenomena. The present system also inspects the amount of bubbles inside the containers, the rate at which they dissolve, and the viscosity of the liquid. The containers may include water, beer, wine, liquid medicine, oil, blood, or any other fluid. The present inspection system uses those counts in a unique manner to predict final static value of liquid level, amount of dissolved gas, and to evaluate liquid viscosity.

After filling at the carousel, the fluid inside the container is in a very active transient condition. This dynamic state is easy to detect. This eliminates the need to shake the container to cause the gas to separate from the fluid.

A measuring system employing a sensor 208 is located a short distance after a filling carousel 205. This system inspects the dynamic processes within each container. This location is used because the fluid inside containers 209 is still active and the bubbles can be easily seen. This location is also especially good for glass containers because they cannot be squeezed to simulate a dynamic condition.

Incoming containers 202 are moving in a direction 201 on an input conveyor 212 to be picked up by the filling carousel. Nozzles 204 on the carousel are used for filling the containers with fluid and dissolved gases. The carousel rotates about axis 206 in clockwise direction 215. The containers leave the carousel on an output conveyor 211. Bottle sensors 203 and 208 are used to correlate a particular container on output conveyor 211 to a specific fill nozzle. Camera 214 and image processor 213 take images of the containers as they move along conveyor 211.

A plurality of images of container 209 are acquired by camera 214 and processor 213, and are stored in the memory (not shown) of processor 213 Camera 214 has a field of view which includes the surface of the container's liquid level as well as the bubbles. This field of view is shown in FIG. 3 and also at 107 FIG. 1. The gray levels of the image are modified to distinguish liquid from bubbles. This is done by selecting a threshold level for liquid and for bubbles and applying a lookup table of the vision system (explained below).

Figure 4:
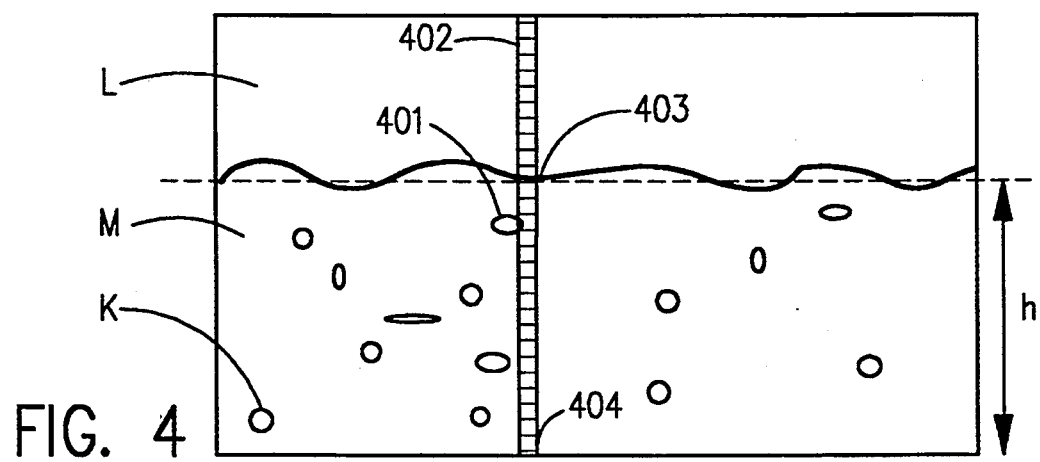
FIG. 4 is a measurement of the fluid's height along one column within the camera's field of view, in accordance with the invention.

The liquid height is measured by counting the number of pixels relating to the fluid along each line (or column) of the modified image (as will be explained in conjunction with FIG. 4 below ). In FIG. 4 the fluid image is modified to have gray levels of value M. Counting of pixels can be performed by the vision system. This is done by using the vision system's histogram feature, i.e., by defining a 'window' or area of interest (AOI) inside an image as one line only. The resultant scan will be a histogram vector which is a count of the number of pixels with equal gray level values. Therefore it is a count of pixels with gray levels of value M, the value to which the fluid image's gray levels were modified. In our case it is the number of pixels of fluid along the vertical line. Another fast way to count pixels while using a vision system like Model 150/151 is described in U.S. Pat. No. 5,204,911, to Schwartz et al. (Apr. 4, 1993), where the template image is an assembly of lines of different gray levels. The template is superposed with a modified image as shown in FIG. 4 or in FIG. 5. The histogram of the superposed images will resolve with the counts of pixels along vertical or horizontal lines. Averaging the count values will indicate the average liquid level.

The bubbles are measured by counting the number of pixels of the bubbles along each line (or column) of the modified image (as be explained in conjunction with FIG. 5 below). Counting of pixels is performed by setting the vision system to define a 'window' or area of interest (AOI) inside an image as one line only. The resultant histogram count will be a vector which is a count of the number of pixels with equal gray level values. Therefore it is a count of pixels with gray levels of value K, the value to which the bubble image's gray levels were modified. In our case it is the number of pixels of bubbles along the vertical or horizontal line. Another fast way to count pixels while using a vision system is defined in our above U.S. Pat. No. 5,204,911, where the template image is an assembly of lines of different gray levels. Averaging the count values will indicate the average liquid level.

Figure 6:
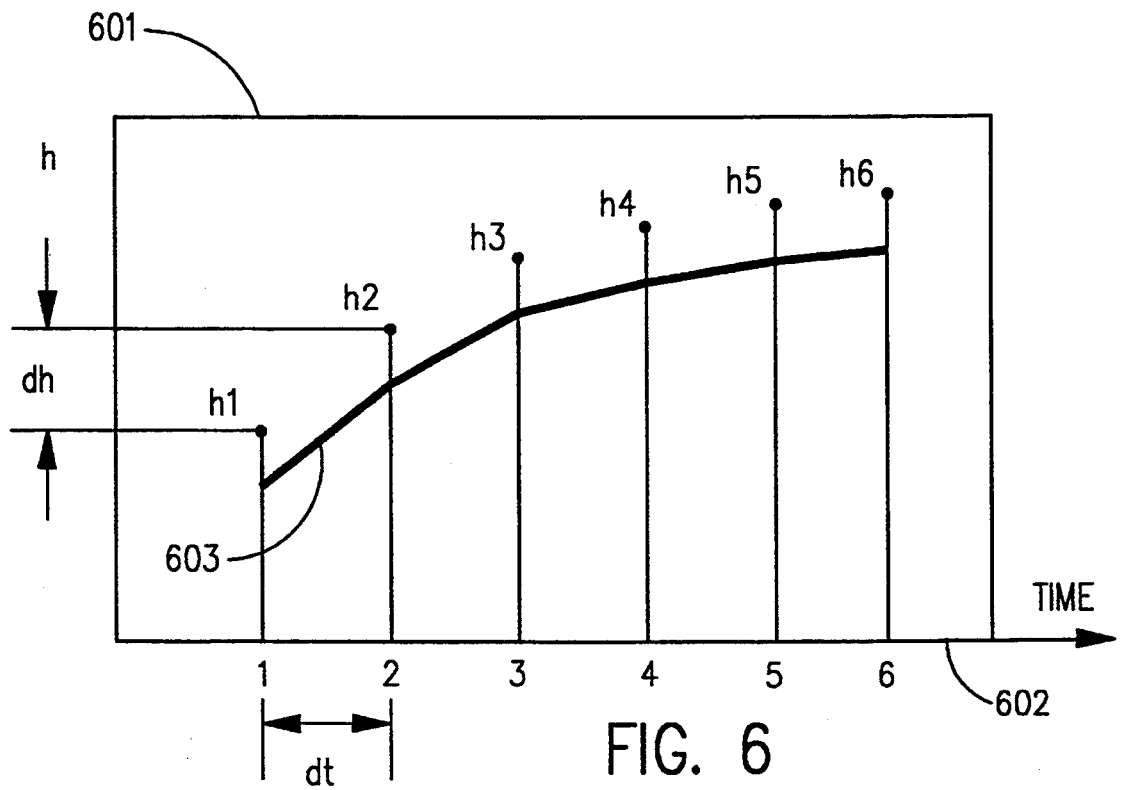
FIG. 6 shows the fluid level height asymptotically approaching a static value, in accordance with the invention.
Figure 7:
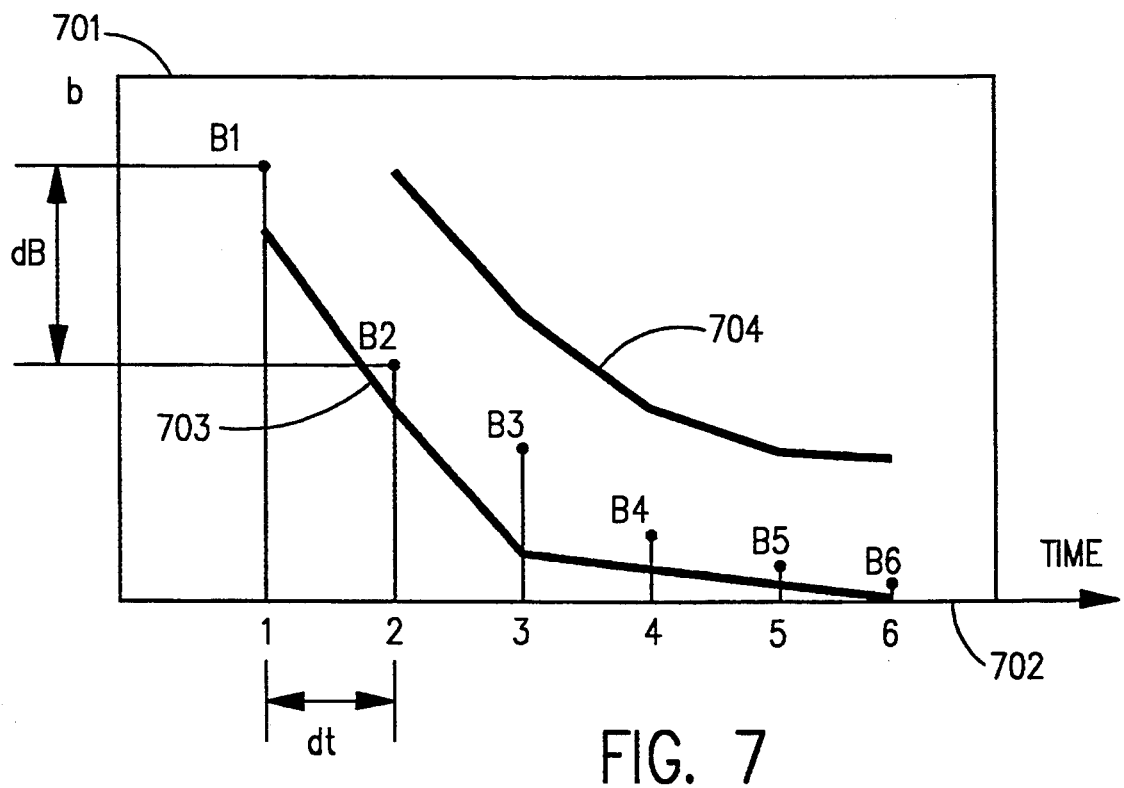
FIG. 7 shows the amount of bubbles asymptotically approaching a static value as they dissolve within the fluid, in accordance with the invention.

The count value indicates the amount of bubbles inside the liquid. Since a plurality of images are acquired, a plot of liquid heights, or amount of bubbles as a function of time is generated (FIGS. 6 and 7). The rate of change of each plot, and a comparison with a good container's behavior, predict the viscosity of the liquid, as well as the existence of any leaks in the container.

Processor 213 counts the number of bubbles, the height of the fluid during a period of time, and then compares the dynamics of each container to determine if the fluid inside behaves within predefined deviations. The results are then compared to a good container's behavior, which has been previously stored in the processor, and are also compared to the operation of other nozzles on the carousel. The sensors enable the quick identification of faulty nozzles which may require adjustment.

Modifying Product Image

Modification of the gray level values of the product image, using lookup tables, is done in real time using existing hardware. The tables are loaded with data during startup of the computer. The data define the conversion function change in real time. For reference see the operating manual, "Lookup Tables" (LUT), Technical Publications Department, 1990, Image Technology, Inc., Woburn, Mass. The lookup tables are used to modify the gray levels of the image. The lookup tables are loaded with a transform function. The transform function is unique for each product and is well known to those skilled in the art. E.g., the transformation function for a beer bottle is as follows: all gray levels in the product image between 0 to 150 (threshold level 150) are converted to gray value 0, and all gray levels between 151 and 255 converted to gray level 160.

Figure 5:
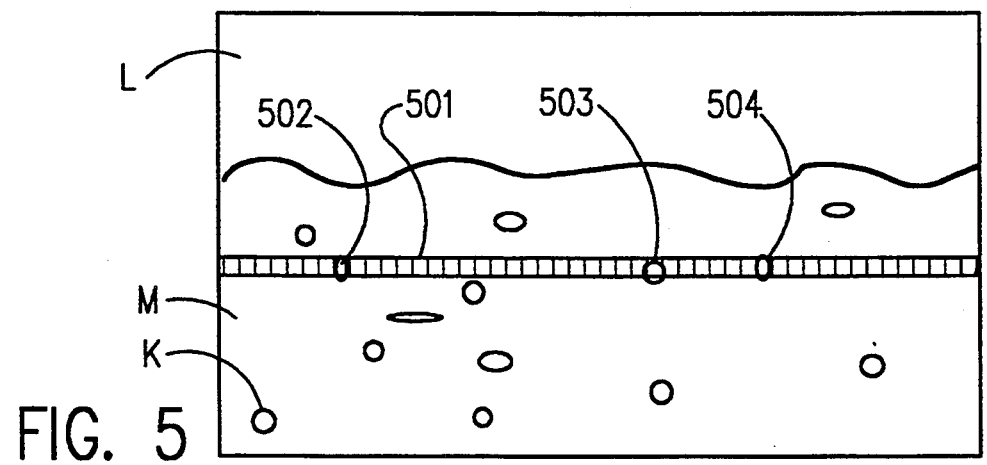
FIG. 5 is a the measurement of the bubbles along one row within the camera's field of view, in accordance with the invention.

The image acquired by camera 214 and shown in FIG. 3 is modified to have bubbles displayed as dark gray levels, as shown in FIGS. 4 and 5. This is done according to the lookup tables. This makes it possible to count pixels related the two groups, pixels related to liquid and pixels related to bubbles. The vision system is able to count liquid height by counting the number of pixels related to the fluid inside the container. Each image is composed of plurality of pixels aligned in columns and rows. The counts takes place along a line which is a column or row in the modified image. The final fluid height is obtained by averaging the counts over the number of lines that pixels were counted, as explained in detail in equations (1) and (2) below.

This modification of the image gray levels is performed with the aid of back light source 215 in FIG. 2. Light rays from source 215 shine toward mirror 210, are reflected from the mirror, pass through the fluid inside the container, and then travel back to camera 214. That makes it possible to have the camera and the light source on the same side of the conveyor, providing mechanical and optical advantages. The camera should be slightly above the light source so that light coming from the container will be collected. A simpler configuration where the camera is on one side of the conveyor and the light source is on the other side of the conveyor is also possible.

FIG. 3—Dynamic State Inside Container

In order to follow the dynamic behavior of a fluid, multiple images of the container are required. Today's computer technology is fast enough to acquire multiple images, and the method described in our above application Ser. No. 07/910,721 is fast enough to perform the image processing in real time.

FIG. 3 illustrates a single image 301, which is field of view 107 of container 102 (FIG. 1), or the neck of container 209 (FIG. 2). Multiple images of container 209 are acquired by camera 214 and are stored in the memory of processor 213 (FIG. 2). Images are acquired at equally spaced times.

The container's fluid level 302 is a wavy line, indicating that the fluid is in a dynamic state. The existence of bubbles 303 also indicates that the fluid is in a dynamic state. The Image gray levels (not shown) contain many gray levels, some representing fluid and others representing bubbles. These gray levels are modified so that the fluid is expressed as one gray level (M, FIG. 4) and the bubbles as another gray level (K, FIG. 4). This is done by selecting a suitable gray level threshold. The selected gray level threshold is the one allowing the maximum number of pixels related to bubbles to be shown in the modified image. If the threshold is not selected right, fewer bubbles are shown in the image. In the example previously given, under "Modifying Product Image", the gray level range was 0 to 255, so that the threshold level must be within this range. First the threshold is selected as value 0. Then it is increased to be of value 1, and so on. In the example previously given, the threshold level was 150. Each time the number of pixels related to bubbles are counted. The threshold with the maximum bubble pixels is selected. All the gray levels above that threshold are converted to one gray level value. All gray levels below that threshold are converted to another gray level value, thereby to form an image with two gray level values. A ternary image with three gray level values is shown in FIG. 4; the gray value K for bubbles, the gray level M for the fluid, and the gray level L for the media above the fluid surface. Another situation occurs when the container includes several types of fluid, layered on top of each other. That case will require a specific gray level value for each type of the layered fluid inside the container. A suitable threshold level is unique to each product and is selected experimentally.

FIG. 4—Measuring Fluid Height In Dynamic State

FIG. 4 is similar to FIG. 3, and is used to demonstrate the procedure of measuring the fluid level height inside a container while the fluid is in a dynamic state.

The gray levels (not shown) of FIG. 3 are modified by the use of the LUTs of processor 213. They appear as shown in FIG. 4, where the bubbles like 401 are darkened and set to a gray level K versus the bubbles in FIG. 3 which have multiple gray levels. Using the same procedure for gray level modification, the gray levels of the fluid (below wavy line 302 in FIG. 3) are modified to be of value M, different that of the air domain (above line 302 in FIG. 3) which is modified to be of a gray level value L. The gray level of the bubbles is different from that of the liquid and from the air domain above the liquid's wavy surface.

A long vertical line 402 is used to calculate fluid height 403. The vision system is selected to scan one vertical line as an area of interest (AOI). The histogram feature is constrained to count pixels within the selected AOI only. The processor is set to move the AOI from line to line to cover the entire body of fluid in real time and in sequential order. Vertical line 402 is a modified image line composed of a row of pixels. E.g., distance between point 403 and point 404 is 25 pixels. This will be the height of the fluid along line 402 in a static state, i.e., a fluid without bubbles.

The fluid is in a dynamic state, and there is a bubble 401 with two pixels long along vertical line 402. The actual height of the fluid will be less than 25 pixels by the height of bubble 401, I.e., 23 pixels only. The processor will count only pixels with gray levels of value M (23 of them) between a bottom point 404 of the image and point 403. Since bubble 401 is two pixels long, i.e., two pixels with gray value K, those pixels are not counted. Therefore the actual height of the fluid along vertical line 402 will be two pixels short of point 403 and equal to 23 pixels.

The procedure will be repeated for all possible vertical lines parallel to line 402 inside the image. An RS170 standard camera can take 512 vertical lines parallel to line 402. The fluid height related to the first vertical line is A1, to the second vertical line is A2, and so on. Each of the counts A1, A2, and so on, are stored in the memory of processor 213. All of the counts are summed by the processor logic unit and divided by the number of counts. The total fluid height is the average height of all of these vertical counts measurements and is expressed as the value h.

$$h = (1/N) \times [A1 + A2 + \ldots + A402 + A512] \quad (1)$$

Where N equals the total number of vertical lines. The value of h is shown in FIG. 4 as the distance in pixels and it expressed the average height of the fluid in a dynamic state.

The h value of the fluid inside the container as a function of time (at successive positions along the production line) is plotted in FIG. 6. Note that the h value rises asymptotically, indicating that the gas in the container is being dissolved and the fluid is reaching its static state.

FIG. 5—Measuring Bubbles In Dynamic State

FIG. 5 is also similar to FIG. 3, and it demonstrates the procedure of measuring the number of bubbles expressed by the number of pixels within a container with the fluid in a dynamic state.

The gray levels of FIG. 3 are modified by the use of the LUTs of processor 213. They appear as shown in FIG. 5, where the bubbles are darkened and set to a specific gray level K versus the ones in FIG. 3 which have multiple gray levels (not shown). The gray level of the bubbles is different from that of the liquid and from the air domain above the liquid's wavy surface. Using the same procedure for gray level modification, the gray levels of the fluid are modified to be of value M, different that of the air domain which has a gray level value L.

A long horizontal line 501 is used to calculate the number of bubbles. The vision system is selected to have one horizontal line as an area of interest (AOI). The processor's histogram feature is set to count pixels within the selected AOI only. The AOI can be moved from line to line to cover the entire body of fluid in real time and in sequential order. Horizontal line 501 is a modified image line composed of a row of pixels. The number of bubbles are expressed as a number of pixels. Bubbles 502, 503, and 504 lie along horizontal line 501, and have gray levels of value K which is different from the gray level M of the fluid. The height of bubble 502 along horizontal line 501 is two pixels, the height of bubble 503 is three pixels, and the height of bubble 504 is two pixels. Processor 106 (FIG. 1), or 213 (FIG. 2) is set to count only pixels with gray level value K. Therefore it will count the number of pixels representing bubbles along horizontal line 501. The count value will be 2+3+2=5 pixels.

The procedure will be repeated for over all horizontal lines parallel to line 501 in the liquid. An RS 170 standard camera can take 480 horizontal lines parallel to line 501. To save processing time, the procedure is repeated only over a preselected number of lines. The number of lines depends upon the type of gas dissolved, the temperature of the liquid, and the pressure inside the container. For a standard beer bottle, the number of lines selected was 20. The total number of pixels representing the amount of bubbles along horizontal line 501 is B501 (B501 equals the number of pixels representing bubble 502, plus those representing bubble 503, plus those representing bubble 504). The amount of bubbles will be decrease with time as the fluid approaches a stable state where the gas is completely dissolved.

The total number of pixels representing the bubbles in the first horizontal line is B1, in the second horizontal line is B2, and so on. Each of the counts B1, B2, and so on, is stored in the memory of the processor 213. All of the counts are summed by the processor logic unit and divided by the number of counts. The total amount of bubbles can be expressed as the average of all of these horizontal count measurements and is expressed as the value B.

$$B = (1/N) \times [B1 + B2 + \ldots + B480] \quad (2)$$

N equals to the total number of horizontal lines on which counts where performed. ( N=480 if camera RS170 is used and if bubbles are counted along all of the horizontal lines).

The total number of pixels representing the bubbles along one row may also be repeatedly counted over a period of time and averaged.

The number of pixels representing bubbles along horizontal line 501 are saved in memory for further analysis.

The value B for the average amount of bubbles as a function of time is plotted in FIG. 7.

FIG. 6—Plot Of Fluid Level In Dynamic State

FIG. 6 is a time plot of the value h from FIG. 4. The value of h, the fluid level's height, was measured six times at equally spaced intervals, as represented by the dots at the tops of the ordinates. The behavior of h is exponential. At the value h=h6, the height of the fluid has reached its static value. The value of h6 can be obtained by extrapolation with time within a small error using the first three values, h1, h2, and h3. The rate of change of value h with time (dh/dt) is a good indicator of the viscosity of the fluid and its ability to hold dissolved gases. I.e., the greater dh/dt, the greater the fluid's viscosity (Measuring beer bottles in one embodiment give dh/dt values of 500, 200, 70, and 10 pixels per 0.5 sec.)

Plot 603 is statistically obtained by inspecting good bottles, i.e., found to be within fluid final acceptance levels. As long as newly inspected bottles have a fluid height behavior above plot 603, the line operator will be assured that the static fluid level height will be within the acceptable range. A higher statistical range (not shown) represents overfilling.

Nozzle 204 on the carousel is adjusted according to the result of FIG. 6. For example, if static height h6 is lower that graph 603, then the opening of nozzle 204 should be increased to allow more fluid to pass into the container.

FIG. 7—Plot Of Bubbles Dissolved In A Dynamic State

FIG. 7 is a time plot of the value B from FIG. 5. The value of B was measured six times at equally spaced intervals. The behavior of B exponentially decays. At the value $B=B6$ the gas in the fluid has reached its static value. The time that it will take the bubbles to dissolve (B6) can be obtained by extrapolation within a small error using the first three values, B1, B2, and B3. The rate of change of value B with time (dB/dt) is a good indicator of the viscosity of the fluid and its ability to hold dissolved gases. I.e., the greater dB/dt, the greater the viscosity of the fluid.

If dB/dt is small, this indicates that there are not enough bubbles in the container. This can be as a result of a leak where bubbles escaped the containers, or it can indicate that not enough gas was injected into the container. Both cases require a rejection of the product. If that situation occurs for the same nozzle, it indicates that the nozzle must be adjusted to inject more gas. It may also indicate a mechanical problem with the nozzle. In both cases the process quality engineer must be alerted.

Plots 703 and 704 are statistically obtained by inspecting good bottles, i.e., those found to be with final acceptance levels for dissolved gases and acceptable product taste (as defined by the manufacturer). As long as newly inspected bottles have bubble behavior between plots 703 and 704, their dissolved gases and tastes will be within the acceptance range.

SUMMARY, RAMIFICATIONS, AND SCOPE

Accordingly, the reader will see that we have provided a method that will enable the inspection of fluid bubbles within a container, as well as the fluid fill level, while both are in a dynamic state. This provides control of the quality of the product (taste of beer and soft drinks) as a function of the number of bubbles. It also provides a method for predicting seal cap leakage by analyzing the exponential decaying of the bubbles to a steady state and estimating and controlling the final fluid level in the container by analyzing the behavior of the fluid's height. We also provide a method for predicting the final static liquid level inside the container by analyzing the behavior of the fluid's height during the dynamic mode. Further, we can correlate the individual bottles with the filling carousel's nozzle to enable specific nozzle adjustment without affecting the whole filling machine. We also provide a way to calibrate the amount of gas that a nozzle injects into the container by inspecting the rate of change of bubbles inside the liquid in a dynamic state. Also by analyzing asymptotic behavior of liquid height and amount of bubbles, we provide viscosity values of liquids.

While the above description contains many specific details, these should not construed as limitations on the scope of the invention, but as exemplification of the presently preferred embodiments thereof. Many other ramifications and variations are possible within the teachings to the invention.

For example, chips of foreign matter such as plastic can be artificially injected in a fluid which is in a dynamic state. By following the movement of those chips and measuring the rate of change of their movement within the liquid at spaced time intervals, we can indirectly inspect the change of viscosity of a fluid which may be under change of pressure or change of temperature. This example basically replaced the inspection of the movement of the bubbles with the movement of the chips.

In another example, we can shake the container to create a dynamic fluid condition inside the container. However this creates a need for extra hardware.

Therefore, the scope of the invention should be determined, not only by examples given, but by the appended claims and their legal equivalents.

We claim:

1. A method for inspecting containers filled with a liquid containing bubbles, while said liquid and said bubbles are in a dynamic state and are moving on a production line, with the use of a sensor and a processing unit having a memory, comprising:
   (a) moving a series of containers along a production line past a filling station and an inspection station,
   (b) filling said series of containers with a liquid at said filling station, said liquid containing bubbles which are suspended in said liquid, said liquid and said suspended bubbles being in a dynamic state as a result of said filling,
   (c) illuminating said containers with light at said inspection station so that resultant light comes from said containers,
   (d) sensing said resultant light coming from said containers with said sensor at said inspection station and converting said resultant light to an electrical signal,
   (e) said containers being illuminated and sensed when said liquid and said suspended bubbles are still in said dynamic state,
   (f) creating, from said electrical signal, a product image comprising a multiplicity of pixels with:
      (1) said pixels having a plurality of intensity levels expressed as a corresponding plurality of respective gray levels,
      (2) a first plurality of said multiplicity of pixels representing said liquid and having gray levels substantially on one side of a predetermined threshold level, and
      (3) a second plurality of said multiplicity of pixels representing said bubbles and having gray levels substantially on the other side of said predetermined threshold level,
   (g) modifying said product image to produce a modified product image so as to distinguish liquid from bubbles by assigning a predetermined single liquid gray level value to all pixels on said one side of said predetermined threshold level, and assigning a predetermined different and single bubble gray level value to all pixels on said other side of said predetermined threshold level, (h) counting the number of pixels having said liquid gray level value and saving the resultant liquid count in memory, (i) counting the number of pixels having said bubble gray level value and saving the resultant bubble pixel count in memory, and (j) analyzing said resultant liquid pixel count and said resultant bubble pixel count for liquid height and bubbles.

2. The method of claim 1, further including analyzing said resultant liquid and bubble counts to determine if said container leaks by comparing said resultant counts with those of an acceptable bottle.

3. The method of claim 1, further including analyzing said resultant liquid and bubble counts by comparing said resultant counts with those of an acceptable bottle.

4. The method of claim 1, further including analyzing said resultant liquid and bubble counts to verify the quantity of bubbles inside said product for quality control by comparing said resultant counts with those of an acceptable bottle.

5. The method of claim 1, further including analyzing said resultant counts for controlling fill nozzle operation by comparing said resultant liquid and bubble counts with those of an acceptable bottle.

6. The method of claim 1, further including analyzing said resultant liquid and bubble counts for controlling fill level height by comparing said resultant counts with those of an acceptable bottle.

7. The method of claim 1 wherein said container contains a liquid selected from the class consisting of beer and soft drinks.

8. The method of claim 1 wherein said container contains a liquid which is water.

9. The method of claim 1 wherein said container contains a liquid which is a liquid medicine.

10. The method of claim 1 wherein said counting the number of pixels having said liquid gray level value is taken along a vertical line of said liquid, said counting the number of pixels having said bubble gray level value is also taken along a vertical line of said liquid, and wherein said analyzing said resultant liquid count and resultant said bubble count is performed by subtracting said resultant bubble count from said resultant liquid count.

11. The method of claim 1 wherein (a) said counting the number of pixels having said liquid gray level value is taken at several successive times to obtain several liquid counts, and further including averaging said several liquid counts to obtain an average liquid count, said average liquid count constituting said resultant liquid count, and (b) said counting the number of pixels having said bubble gray level value is taken at several successive times to obtain several bubble counts, and further including averaging said several bubble counts to obtain an average bubble count, said average bubble count constituting said resultant bubble count.

12. The method of claim 1 wherein said counting the number of pixels having said liquid gray level value is taken along a vertical line of said liquid and said counting the number of pixels having said bubble gray level value is also taken along a vertical line of said liquid and wherein said analyzing said resultant liquid count and resultant said bubble count is performed by subtracting said resultant bubble count from said resultant liquid count.

13. A system for inspecting containers filled with a liquid containing bubbles, while said liquid and said bubbles are in a dynamic state and are moving on a production line, with the use of a sensor and a processing unit having a memory, comprising:

(a) a production line comprising a filling station and an inspection station, (b) moving means for moving a series of containers along said production line past said filling station and said inspection station, (c) filling means at said filling station for filling said containers with a liquid containing suspended bubbles, said liquid and said suspended bubbles being in a dynamic state as a result of said filling, (d) illuminating means at said inspection station for illuminating said containers with light so that resultant light comes from each of said containers, (e) sensing and converting means at said inspection station for (a) sensing said resultant light coming from said one of said containers, said sensing and converting means including said sensor, and (b) converting said resultant light to an electrical signal, (f) said illuminating means illuminating said containers with light, and said sensing and converting means sensing said resultant light coming from said containers, when said liquid and said suspended bubbles are still in said dynamic state, (g) image means for creating, from said electrical signal, a product image comprising a multiplicity of pixels, said image means arranged to cause said pixels to have a plurality of intensity levels expressed as a corresponding plurality of respective gray levels, with a first plurality of said multiplicity of pixels representing said liquid and having gray levels substantially on one side of a predetermined threshold level, and a second plurality of said multiplicity of pixels representing said bubbles and having gray levels substantially on the other side of said predetermined threshold level, (h) modifying means for modifying said product image to produce a modified product image so as to distinguish liquid from bubbles by assigning a predetermined single liquid gray level value to all pixels on said one side of said predetermined threshold level, and assigning a predetermined different and single bubble gray level value to all pixels on said other side of said predetermined threshold level, (i) liquid pixel counting means for counting the number of pixels having said liquid gray level value and saving the resultant liquid pixel count in memory, (j) bubble pixel counting means for counting the number of pixels having said bubble gray level value and saving the resultant bubble pixel count in memory, and (k) analyzing means for analyzing said resultant liquid pixel count and said resultant bubble pixel count for liquid height and bubbles.

14. The system of claim 13, further including means for analyzing said liquid and bubble counts to determine if said container leaks by comparing said liquid and bubble counts with those of an acceptable bottle.

15. The system of claim 13, further including means for analyzing said liquid and bubble counts by comparing said liquid and bubble counts with those of an acceptable bottle.

16. The system of claim 13, further including means for analyzing said liquid and bubble counts to verify the quantity of bubbles inside said product for quality control by comparing said liquid and bubble counts with those of an acceptable bottle.

17. The system of claim 13, further including means for analyzing said liquid and bubble counts for controlling fill nozzle operation by comparing said liquid and bubble counts with that of an acceptable bottle.

18. The system of claim 13, further including analyzing said liquid and bubble counts for controlling fill level height by comparing said liquid and bubble counts with those of an acceptable bottle.

19. The system of claim 13 wherein said liquid pixel counting means is arranged to count the pixels along a vertical line of said liquid and said bubble pixel counting means is also taken along a vertical line of said liquid, and wherein said analyzing means is arranged to subtract said resultant bubble pixel count from said resultant liquid pixel count.

20. The system of claim 13 wherein said liquid pixel counting means is arranged to take several liquid counts at successive times and average the counts and wherein said bubble pixel counting means is arranged to take several bubble counts at successive times and average the resultant count.

* * * * *